United States Patent
Oh et al.

(10) Patent No.: US 10,520,470 B2
(45) Date of Patent: Dec. 31, 2019

(54) TEMPERATURE COMPENSATION METHOD FOR GAS SENSOR MODULE USING CHANGE OF HEATER CURRENT

(71) Applicants: Hyundai Motor Company, Seoul (KR); Kia Motors Corporation, Seoul (KR); NANOIONICS KOREA CO., LTD., Gangneung-si (KR)

(72) Inventors: Sun-Mi Oh, Bucheon-si (KR); Hyun-Soo Sohn, Suwon-si (KR); Jong-Min Kwon, Gunpo-si (KR); Yang-Ki Kim, Seoul (KR); Tae-Won Lee, Seoul (KR); Ji-Hye Kim, Seoul (KR)

(73) Assignees: Hyundai Motor Company, Seoul (KR); Kia Motors Corporation, Seoul (KR); NANOIONICS KOREA CO., LTD., Gangneung-si (KR)

( * ) Notice: Subject to any disclaimer, the term of this patent is extended or adjusted under 35 U.S.C. 154(b) by 108 days.

(21) Appl. No.: 15/793,739

(22) Filed: Oct. 25, 2017

(65) Prior Publication Data

US 2018/0266988 A1 Sep. 20, 2018

(30) Foreign Application Priority Data

Mar. 16, 2017 (KR) .......................... 10-2017-0032978

(51) Int. Cl.
*G01N 27/41* (2006.01)
*G01N 27/417* (2006.01)
(Continued)

(52) U.S. Cl.
CPC ......... *G01N 27/4175* (2013.01); *G01N 25/18* (2013.01); *G01N 27/14* (2013.01); *G01N 27/18* (2013.01)

(58) Field of Classification Search
CPC .... G01N 27/4175; G01N 25/18; G01N 27/14; G01N 27/18
(Continued)

(56) References Cited

U.S. PATENT DOCUMENTS 9,429,541 B2 8/2016 Yoshida et al.

FOREIGN PATENT DOCUMENTS

| JP | 2015-045546 A | 3/2015 |
|---|---|---|
| JP | 2016-011928 A | 1/2016 |

(Continued)

*Primary Examiner* — Tarun Sinha
(74) *Attorney, Agent, or Firm* — Morgan, Lewis & Bockius LLP (57) ABSTRACT

A temperature compensation method for a gas sensor module using a change of heater current, may include deriving an output voltage equation of the gas sensor module from a cell reaction equation of an electrolyte and deriving the output voltage equation to an equation for a fluctuation temperature which varies depending on a sensor temperature and an unknown type compensation coefficient; deriving the fluctuation temperature to heater current indicating a current value of a heater formed in the gas sensor module and deriving the output voltage equation by the heater current and the compensation coefficient; and measuring output voltage depending on current of heaters at two or more points to determine the compensation coefficient of the output voltage equation, and the output voltage is configured to be compensated with the change of the heater current measured by the gas sensor module regardless of an external temperature.

5 Claims, 6 Drawing Sheets

(51) Int. Cl.
  *G01N 25/18*  (2006.01)
  *G01N 27/14*  (2006.01)
  *G01N 27/18*  (2006.01)
(58) Field of Classification Search
  USPC .......................................................... 73/25.1
  See application file for complete search history.

(56) References Cited

FOREIGN PATENT DOCUMENTS

| | | |
|---|---|---|
| KR | 10-2009-0056731 A | 6/2009 |
| KR | 10-2009-0083125 A | 8/2009 |

TEMPERATURE COMPENSATION METHOD FOR GAS SENSOR MODULE USING CHANGE OF HEATER CURRENT

CROSS-REFERENCE(S) TO RELATED APPLICATIONS

The present application claims priority to Korean Patent Application No. 10-2017-0032978, filed on Mar. 16, 2017, the entire contents of which is incorporated herein for all purposes by this reference.

BACKGROUND OF THE INVENTION

Field of the Invention

The present invention relates to a temperature compensation method for a gas sensor module using a change of heater current, and particularly, to a compensation method for compensating an output voltage by measuring a resistance or current of a heater disposed in a gas sensor module.

Description of Related Art

Carbon dioxide as a gas is chemically very stable in the atmosphere and is a primary cause of global warming. The need for controlling the concentration of carbon dioxide has increased for indoor air-conditioning of a building and horticulture in addition to an environmental issue, and as a result, research into a method for measuring the concentration of carbon dioxide gas which exists in the atmosphere has been actively conducted.

As the method for measuring the concentration of the carbon dioxide gas which exists in the atmosphere at present, an optical method (NDIR scheme) is provided and the present scheme is a scheme that measures the concentration of carbon dioxide by measuring an absorption degree of infrared rays using a principle in which the carbon dioxide absorbs only infrared rays having a specific wavelength. Further, a solid electrolyte or semiconductor type gas sensor also exists and a detecting principle of the semiconductor type gas sensor adopts a phenomenon (a change in electric conductivity, that is, resistance or thermal conductivity) induced as target gas is adsorbed on or desorbed on the surface of a ceramic (oxide) semiconductor.

In the present regard, Korean Patent Unexamined Publication No. 10-2009-0083125 (TEMPERATURE-COMPENSATED GAS MEASUREMENT APPARATUS FOR NANO DEVICE GAS SENSOR) in the related art discloses a gas measurement apparatus using a nano-device gas sensor, which can accurately compensate a resistance value in the gas measurement apparatus which is changed depending on a temperature, and verify a temperature compensation degree and whether a circuit malfunctions.

However, in the related art, there is a problem in that since analog circuits including a Wheatstone bridge, etc., are required in the gas sensor and the temperature is directly compensated by measuring the change in temperature in the gas sensor, a high-priced temperature sensor is particularly required.

The information disclosed in this Background of the Invention section is only for enhancement of understanding of the general background of the invention and should not be taken as an acknowledgement or any form of suggestion that this information forms the prior art already known to a person skilled in the art.

BRIEF SUMMARY

Various aspects of the present invention are directed to providing a compensation method of a gas sensor module, which compensates a temperature without an internal temperature sensor.

Various aspects of the present invention are directed to providing a temperature compensation method for a gas sensor module using a change of heater current, including: a first step of deriving an output voltage equation of the gas sensor module from a cell reaction equation of an electrolyte, and deriving the output voltage equation to an equation for a fluctuation temperature which varies depending on a sensor temperature and an unknown type compensation coefficient; a second step of deriving the fluctuation temperature by the heater current indicating a current value of a heater formed in the gas sensor module, and deriving the output voltage equation by the heater current and the compensation coefficient; and a third step of measuring the output voltage depending on the current of heaters at two or more points to determine the compensation coefficient of the output voltage equation, and the output voltage is compensated with the change of the heater current measured by the gas sensor module regardless of an external temperature.

In the first step, the cell reaction equation of the electrolyte may be expressed by an electrode reaction energy equation to be derived to an equation associated with electrode reaction enthalpy or entropy.

The second step may include deriving a fluctuation resistance of the heater depending on the fluctuation temperature, and deriving a relationship equation of the heater current and the output voltage by use of the fluctuation resistance.

The third step may include determining a final compensation equation by substituting the compensation coefficient in the output voltage equation, and the output voltage which fluctuates may be compensated by measuring the heater current changed depending on the fluctuation temperature through the final compensation equation.

The output voltage may be derived by a primary linear equation depending on the fluctuation temperature.

According to an exemplary embodiment of the present invention, since a temperature is compensated by the heater resistance, a separate thermometer need not be attached, reducing cost.

Since a separate temperature measurement circuit is not required and a heater itself contacts a sensor, there is an advantage that a temperature change of a sensor can be rapidly observed.

The methods and apparatuses of the present invention have other features and advantages which will be apparent from or are set forth in more detail in the accompanying drawings, which are incorporated herein, and the following Detailed Description, which together serve to explain certain principles of the present invention.

It should be understood that the appended drawings are not necessarily to scale, presenting a somewhat simplified representation of various features illustrative of the basic principles of the invention. The specific design features of the present invention as disclosed herein, including, for example, specific dimensions, orientations, locations, and shapes will be determined in part by the particular intended application and use environment.

In the figures, reference numbers refer to the same or equivalent parts of the present invention throughout the several figures of the drawing.

DETAILED DESCRIPTION

Reference will now be made in detail to various embodiments of the present invention(s), examples of which are illustrated in the accompanying drawings and described below. While the invention(s) will be described in conjunction with exemplary embodiments, it will be understood that the present description is not intended to limit the invention(s) to those exemplary embodiments. On the contrary, the invention(s) is/are intended to cover not only the exemplary embodiments, but also various alternatives, modifications, equivalents and other embodiments, which may be included within the spirit and scope of the invention as defined by the claims.

Further, in the following description, a detailed explanation of known technologies associated with the present invention may be omitted to avoid unnecessarily obscuring the subject matter of the present invention.

Figure 1:
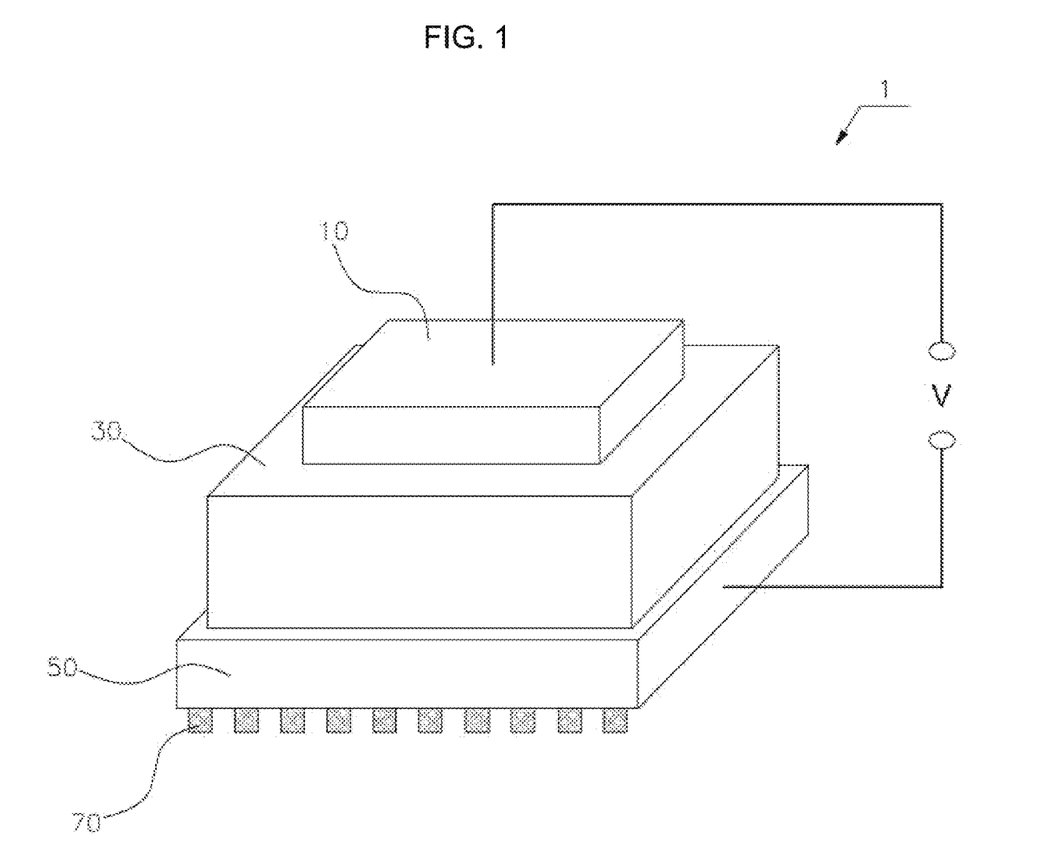
FIG. 1 illustrates a gas sensor module adopting temperature compensation according to an exemplary embodiment of the present invention.

FIG. 1 illustrates a gas sensor module 1 adopting temperature compensation according to an exemplary embodiment of the present invention. Referring to FIG. 1, the gas sensor module 1 may include a detecting electrode 10, a reference electrode 50, an electrolyte 30, and a heater 70.

In a solid electrolyte gas sensor, ions in a solid move along a solid electrolyte for a chemical balance by gas contacting the surface of the solid and the concentration of the contact gas may be measured by use of a potential difference between both end portions of the solid, which occurs at that time.

The solid electrolyte represents a material in which current may flow by movement of the ions in a solid state, and in the exemplary embodiment of the present invention the solid electrolyte may be any one of zirconia, Na-beta-alumina, NASICON, and LISICON.

The electrolyte 30 exists between the detecting electrode 10 and the reference electrode 50 and may be expressed by a sensitivity that indicates a sensibility degree of a measurement apparatus, a receiver, etc., which react with external stimuli and actions. A difference of electromotive force depending on a change of the concentration of measurement gas is defined as an output voltage in an exemplary embodiment of the present invention.

In the exemplary embodiment of the present invention, the change of the output voltage needs to sensed, which is caused due to a chemical reaction between a gas to be measured and a detected material, and as an operating temperature a high temperature required for a detected material decomposition reaction is required. In such a process, the high temperature required for operating the sensor may be defined as the operating temperature and to the present end, the gas sensor module may include the heater 70.

The output voltage may be defined as an electrochemical potential difference between the detecting electrode 10 and the reference electrode 50, and represents the potential difference between the reference electrode 50 and the detecting electrode 10.

According to another exemplary embodiment, the gas sensor module 1 may include a heater device, a compensation device, or a control device and the heater device may include a device of which a resistance or consumption current is changed depending on an external temperature, the compensation device may determine a compensation coefficient by determining the change amount of the output voltage depending on the change amount of the resistance or the consumption current of the heater device, and the control device may control the output voltage so that the compensated output voltage is shown depending on the external temperature by use of the compensation coefficient of the compensation device.

The gas sensor module 1 may compensate the output voltage by the compensation method to be described below and compensate the output voltage by the change of the current of the heater 70, which is measured in the gas sensor module 1 regardless of the external temperature.

Hereinafter, a temperature compensation method for the gas sensor module 1 by measuring a change in resistance or current of the heater 70 formed in the gas sensor module 1 will be described.

Figure 2:
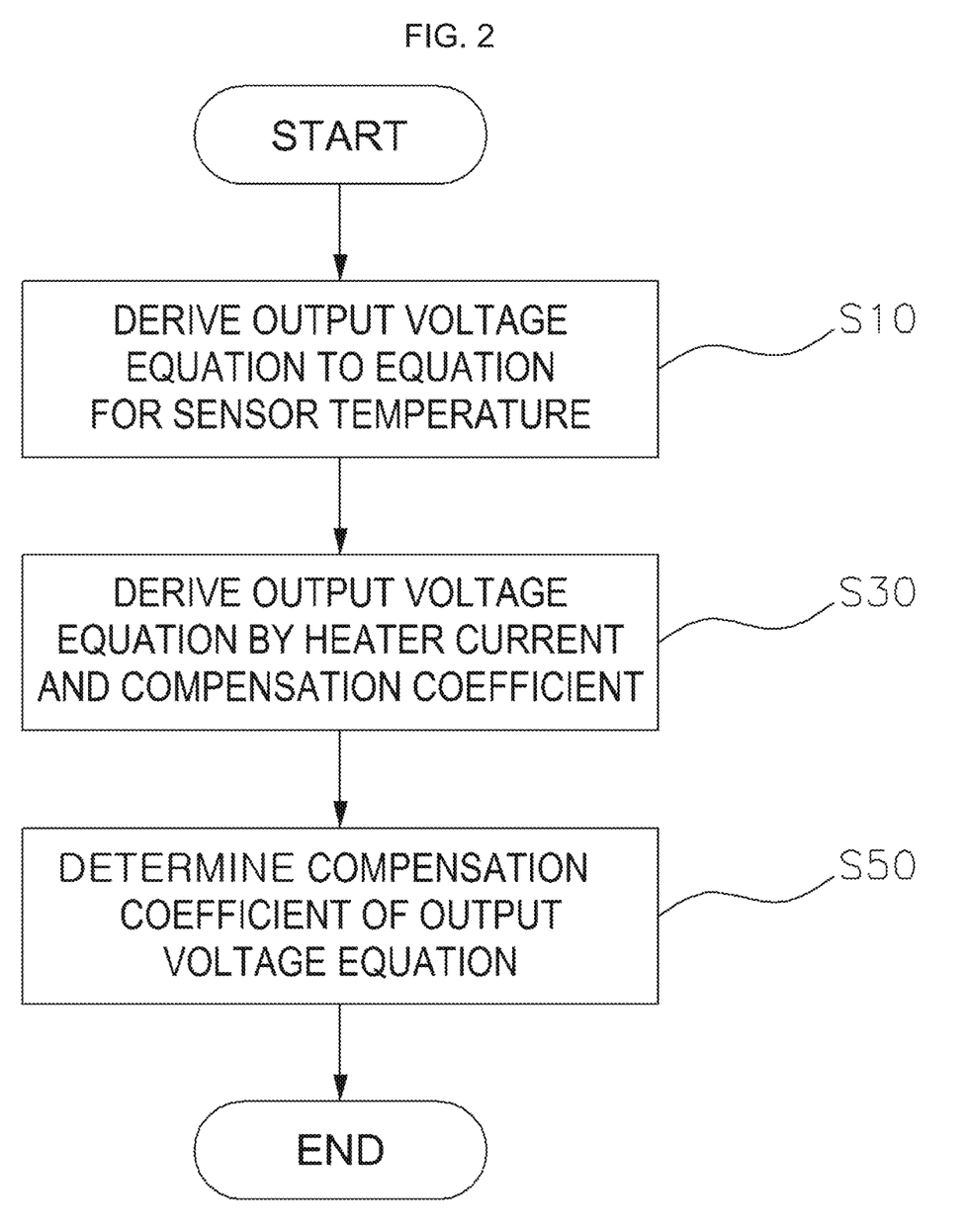
FIG. 2 is a flowchart of a temperature compensation method for a gas sensor module using a change of heater current according to an exemplary embodiment of the present invention.

FIG. 2 is a flowchart of a temperature compensation method for the gas sensor module 1 using a change of current of the heater 70 according to an exemplary embodiment of the present invention. Referring to FIG. 2, the temperature compensation method for the gas sensor module 1 may include a first step, a second step, and a third step.

In the first step (S10), an output voltage equation of the gas sensor module 1 may be derived from a cell reaction equation of the electrolyte 30 and the output voltage equation may be derived to an equation for a variation temperature which varies depending on a sensor temperature and an unknown type compensation coefficient.

When the NASICON is used as the electrolyte 30, output voltage V of FIG. 1 may be expressed through a chemical reaction equation given below:

Detecting electrode: $2Na^+_{detecting} + CO_2 + (1/2)O_2 = Na_2CO_3$
Reference electrode: $2Na^+_{reference} + (1/2)O_2 = Na_2O_{NASICON}$
Whole electrode reaction: $Na_2O + CO_2 = Na_2CO_3$ In the first step (S10), the cell reaction equation of the electrolyte 30 is expressed by an electrode reaction energy (Gibbs energy) equation to be derived to an equation associated with electrode reaction enthalpy or entropy. Herein, the output voltage may be derived as shown in [Equation 1].

[Equation 1]

($\Delta G^f$: formation free energy, $\Delta G^{rxn}$: Reaction energy of whole electrode reaction, $a_{CO_2}$: carbon dioxide activity/concentration, $\Delta H^{rxn}$:

$$\Delta G^{rxn} = \Delta G^f_{Na_2O} + \Delta G^f_{CO_2} - \Delta G^f_{Na_2CO_2}$$

$$V = -\frac{RT}{2F}\ln a_{CO_2} + \frac{1}{2F}\Delta G^{rxn}$$

$$= -\frac{\ln 10 \times RT}{2F}\log a_{CO_2} + \frac{1}{2F}(\Delta H^{rxn} - T\Delta S^{rxn})$$

total electrode reaction enthalpy (almost regardless of the temperature), $\Delta S^{rxn}$: total electrode reaction entropy (regardless of the temperature), T: temperature, R: gas constant, F: Faraday constant, V: sensor output voltage)

In Equation 1 given above, the cell reaction equation of the electrolyte 30 is shown as the electrode reaction energy equation and respective energy equations are expressed as the equation for the Gibbs free energy. In Equation 1 given above, each reaction enthalpy and entropy may be expressed as a function for a temperature which influences the gas sensor.

The temperature shown in Equation 1 may be acquired by measuring the temperature of the heater 70, which fluctuates depending on the external temperature, but in an exemplary embodiment of the present invention, since a thermometer is not required, the temperature in Equation 1 may be acquired through the change of the current or resistance of the heater 70.

When the output voltage is again expressed by a reference temperature and a fluctuation temperature in Equation 1, the output voltage may be expressed as follows.

$$V = -\frac{\ln 10 \times RT}{2F}\log a_{CO_2} + \frac{1}{2F}(\Delta H^{rxn} - T\Delta S^{rxn})$$

Total output voltage may be determined as shown in Equation 2 from the above equation.

$$V^0 = -\frac{\ln 10 \times RT^0}{2F}\log a_{CO_2} + \frac{1}{2F}(\Delta H^{rxn} - T^0\Delta S^{rxn})$$

$$V = V^0 + \Delta V \quad \text{[Equation 2]}$$

$$= -\frac{\ln 10 \times R(T^0 + \Delta T)}{2F}\log C_{CO_2} +$$

$$\frac{1}{2F}(\Delta H^{rxn} - (T^0 + \Delta T)\Delta S^{rxn})$$

$$= A\left(\frac{T^0 + \Delta T}{T^0}\right)\log C_{CO_2} + B'(T^0 + \Delta T) + C'$$

$$= (A\log C_{CO_2} + B) + \left(\frac{A\Delta T}{T^0}\log C_{CO_2} + B'\Delta T\right)$$

($\Delta G^f$: formation free energy, $\Delta G^{rxn}$: Reaction energy of whole electrode reaction, $a_{CO_2}$: carbon dioxide activity/concentration, $\Delta H^{rxn}$: total $\Delta G^{rxn} = \Delta G^f_{Na_2O} + \Delta G^f_{CO_2} - \Delta G^f_{Na_2CO_3}$ electrode reaction enthalpy (almost regardless of the temperature), $\Delta S^{rxn}$: total electrode reaction entropy (almost regardless of the temperature), T: sensor temperature, R: gas constant, F: Faraday constant, V: sensor output voltage, A: sensitivity at the reference temperature, B, B',C',D: constant, T0: reference temperature (sensor temperature at a specific outdoor temperature (e.g., 23° C.), V0: output voltage at the reference temperature, $\Delta V$: output voltage change amount depending on the outdoor temperature)

Figure 3A:
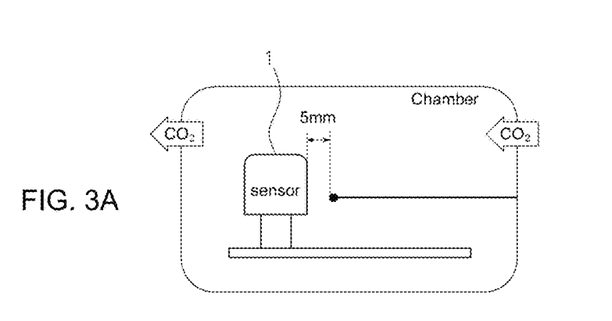
FIG. 3A illustrates a case where gas is measured with a gas sensor module by setting an environmental condition in a chamber according to an exemplary embodiment of the present invention.

FIG. 3A illustrates a case where gas is measured with a gas sensor module 1 by setting an environmental condition in a chamber according to an exemplary embodiment of the present invention. Referring to FIG. 3A, a chamber volume of 150 mL, a gas flow of 100 sccm, a humidity control of a mixture of Wet Air and Dry Air, $CO_2$ concentration control of a mixture of Air/$CO_2$-air balance, external temperature control of a Kanthal furnace, and the thermometer of a K-type TC may be determined according to the exemplary embodiment of the present invention.

In the second step (S30), the fluctuation temperature may be derived by the current of the heater 70, which indicates a current value of the heater 70 formed in the gas sensor module 1 and the output voltage equation may be derived by the current of the heater 70 and the compensation coefficient. Therefore, in Equation 2 given above, a former term may become $V^0$ as reference voltage and a latter term may become $\Delta V$ and the latter term may be derived to the fluctuation temperature.

Figure 3B:
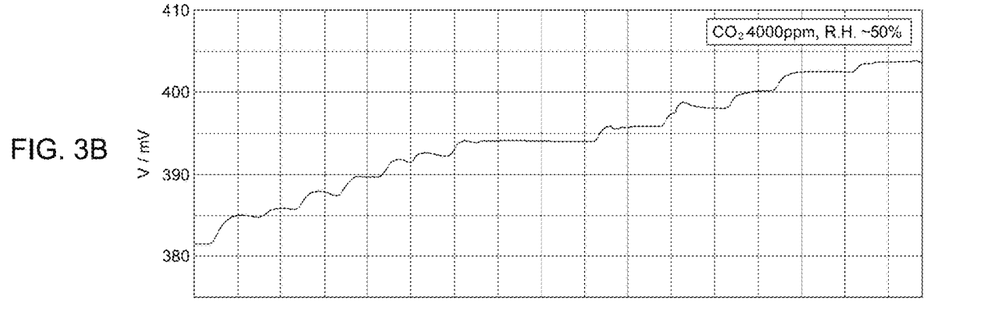
FIG. 3B illustrates output voltage depending on an external temperature according to an exemplary embodiment of the present invention.
Figure 3C:
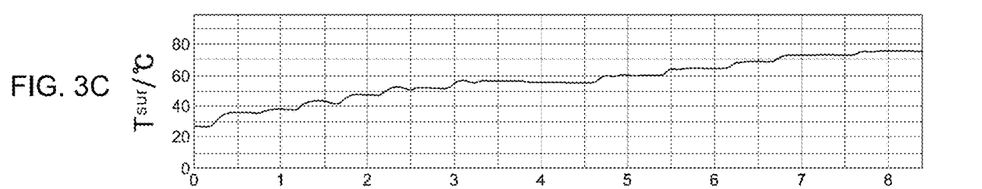
FIG. 3C illustrates a case where the external temperature increases with time according to an exemplary embodiment of the present invention.
Figure 3D:
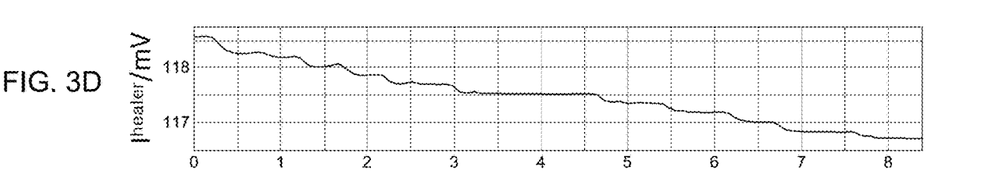
FIG. 3D illustrates a current consumption amount of a heater depending on the external temperature according to an exemplary embodiment of the present invention.

FIG. 3B, FIG. 3C, and FIG. 3D illustrate the output voltage depending on the external temperature and the consumption current of the heater 70 according to the exemplary embodiment of the present invention. As illustrated in FIG. 3C, the external temperature may be changed in the range of 25° C. to 75° C. according to the exemplary embodiment, and as a result, the output voltage is shown in FIG. 3B and the consumption current of the heater 70 may fluctuate as shown in FIG. 3D.

The present invention is used for compensating the output voltage without a thermometer and in Equation 2, the equation for the resistance or current for the heater 70 may be derived to measure the fluctuation temperature.

The second step (S30) may include deriving the fluctuation resistance of the heater 70 depending on the fluctuation temperature, and deriving a relationship equation of the current of the heater 70 and the output voltage using the fluctuation resistance.

The deriving of the fluctuation resistance of the heater 70 depending on the fluctuation temperature may be derived from Equation 3. As an equation for general temperature and resistance, it can be seen that resistivity is changed in the gas sensor module 1 depending on the fluctuation temperature generated outside the gas sensor module 1, and as a result, the output voltage may be derived to be predicted only by measuring the current of the heater 70 in the gas sensor module 1.

$$\frac{\Delta \rho}{\rho} = \alpha \Delta T \quad \text{[Equation 3]}$$

($\rho$: resistivity, T: temperature, $\alpha$: temperature coefficient)
Equation 4 may be derived as below based on Equation 3.

$$\frac{\Delta \rho}{\rho} = \alpha \Delta T; V^{heater} = I^{heater} \times S \times \rho$$

$$\rho = (V^{heater} \times S^{-1}) \times (I^{heater})^{-1};$$

$$\frac{\Delta \rho}{\rho} = \alpha \Delta T \rightarrow \frac{\partial \rho}{\rho} = \alpha \partial T - \left(\frac{\partial I^{heater}}{I^{heater}}\right)_{V^{heater}} = \alpha \partial T$$

($\alpha$, almost constant under a condition of a change in outdoor temperature, the change amount of $I^{heater}$ is approximately several %, S: shape coefficient)

$$\left.\frac{\partial T}{\partial I^{heater}}\right)_{V^{heater}} = -(\alpha \times I^{heater})^{-1} \approx D \quad \text{[Equation 4]}$$

($\alpha$, almost constant under a condition of a change in outdoor temperature, the change amount of $I^{heater}$ is approximately several %, D: constant)

$$\Delta T \approx D \Delta I^{heater} \quad \text{[Equation 5]}$$

Therefore, the shape coefficient in the heater 70 and the consumption current of the heater 70 are determined and Equation 5 may be derived from Ohm's law. Since the fluctuation temperature and the change of the current of the heater 70 are almost linear, the output voltage may also be derived by a primary linear equation depending on the fluctuation temperature.

Deriving the relationship equation of the current of the heater 70 and the output voltage by use of the fluctuation resistance may be derived by substituting Equation 5 into Equation 2. The output voltage value may be expressed as the current of the heater 70 in Equation 2 through the relationship between the fluctuation temperature and the fluctuation resistance and the relationship between the fluctuation resistance and the current of the heater 70. Therefore, the fluctuation of the output voltage may be derived as shown in Equation 6.

$$\Delta V = \left(\frac{A}{T^0}\log C_{CO_2} + B'\right) \times D \times \Delta I^{heater} \quad \text{[Equation 6]}$$

Figure 4:
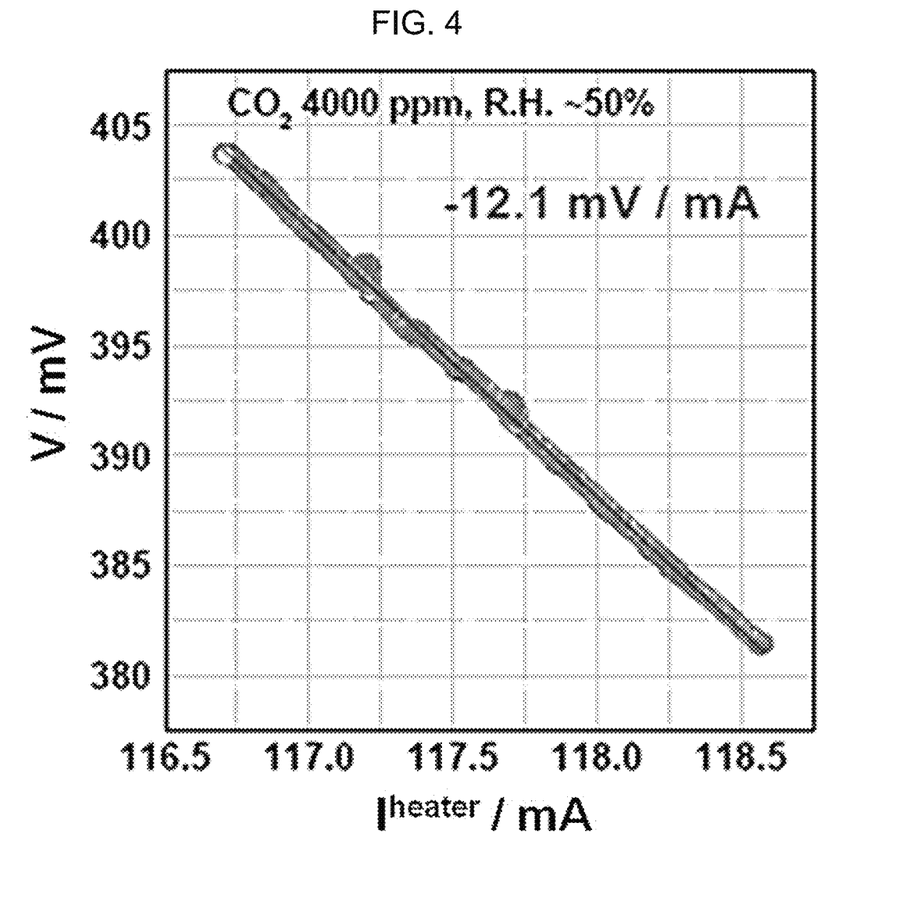
FIG. 4 illustrates output voltage of a gas sensor module to consumption current of the heater according to an exemplary embodiment of the present invention.
Figure 5:
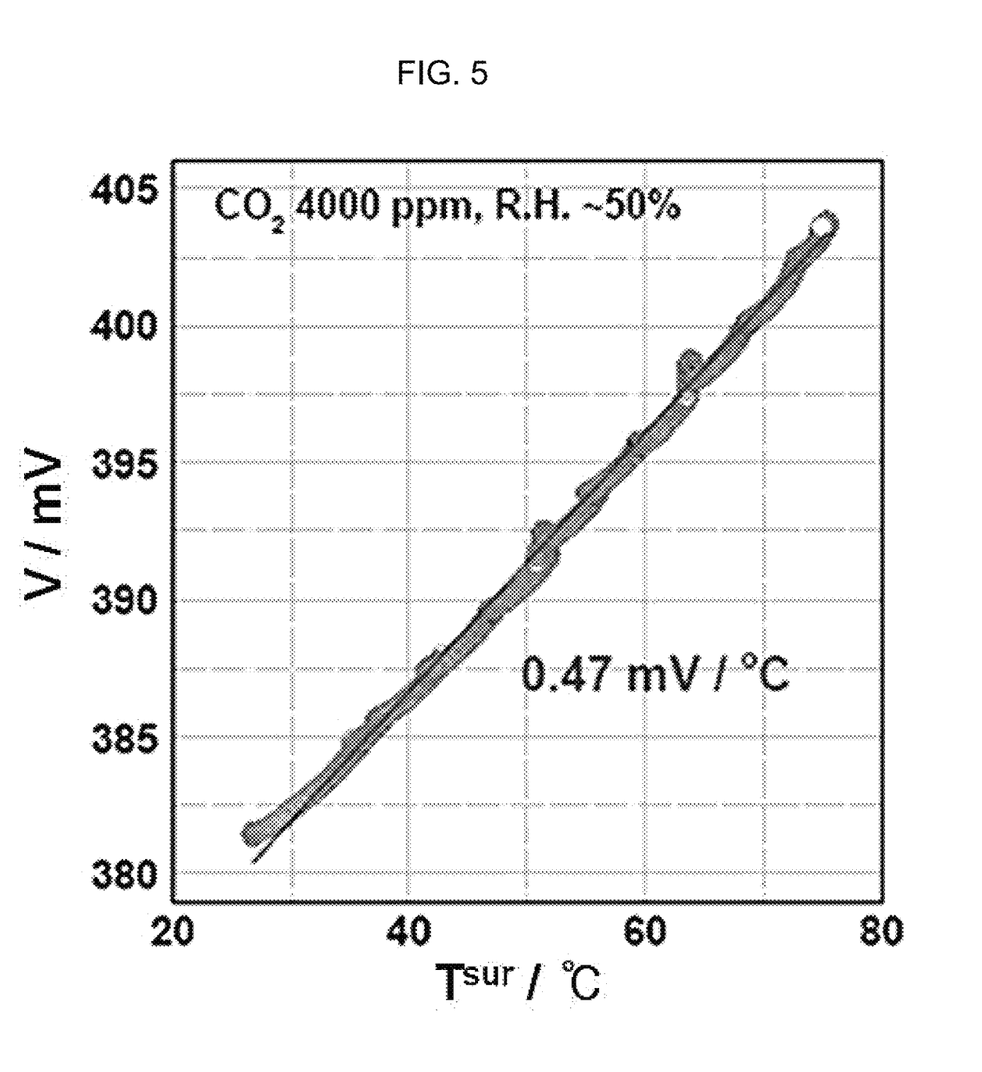
FIG. 5 illustrates the output voltage of the gas sensor module depending on the external temperature according to the exemplary embodiment of the present invention.

FIG. 4 and FIG. 5 illustrate the output voltage of the gas sensor module 1 to the consumption current of the heater 70 and the output voltage to the external temperature according to an exemplary embodiment of the present invention. The output of Equation 6 given above may be clearly appreciated with reference to FIG. 4 and FIG. 5.

In the third step (S50), the output voltage depending on the current of the heaters 70 at two or more points is measured to determine the compensation coefficient of the output voltage equation. The third step may include determining a final compensation equation by substituting the compensation coefficient in the output voltage equation and the output voltage which fluctuates may be compensated by measuring the current of the heater 70, which is changed depending on the fluctuation temperature through the final compensation equation.

The consumption current of the heater 70 and the output voltage show the linear relationship due to the change of the external temperature. Referring to Equation 6, B' and D may be a change rate of the sensor output voltage to the current of the heater 70 at two carbon dioxide concentrations.

$$C_{CO_2} = 10^{\left[\frac{V - (B + B' \times D \times \Delta I^{heater})}{A\left(1 + \frac{D \times \Delta I^{heater}}{T^0}\right)}\right]} \quad \text{[Equation 7]}$$

($\Delta I^{heater} = I^{heater} - I^{heater,0}$, V: sensor output voltage, $I^{heater}$: heater current consumption amount, $I^{heater,0}$: reference current, current consumption amount at the reference temperature, $T^0$: reference temperature, sensor temperature at the reference current, A: sensitivity (approximately −60 mV/decade) at the reference temperature (alternatively, reference current))

Figure 6:
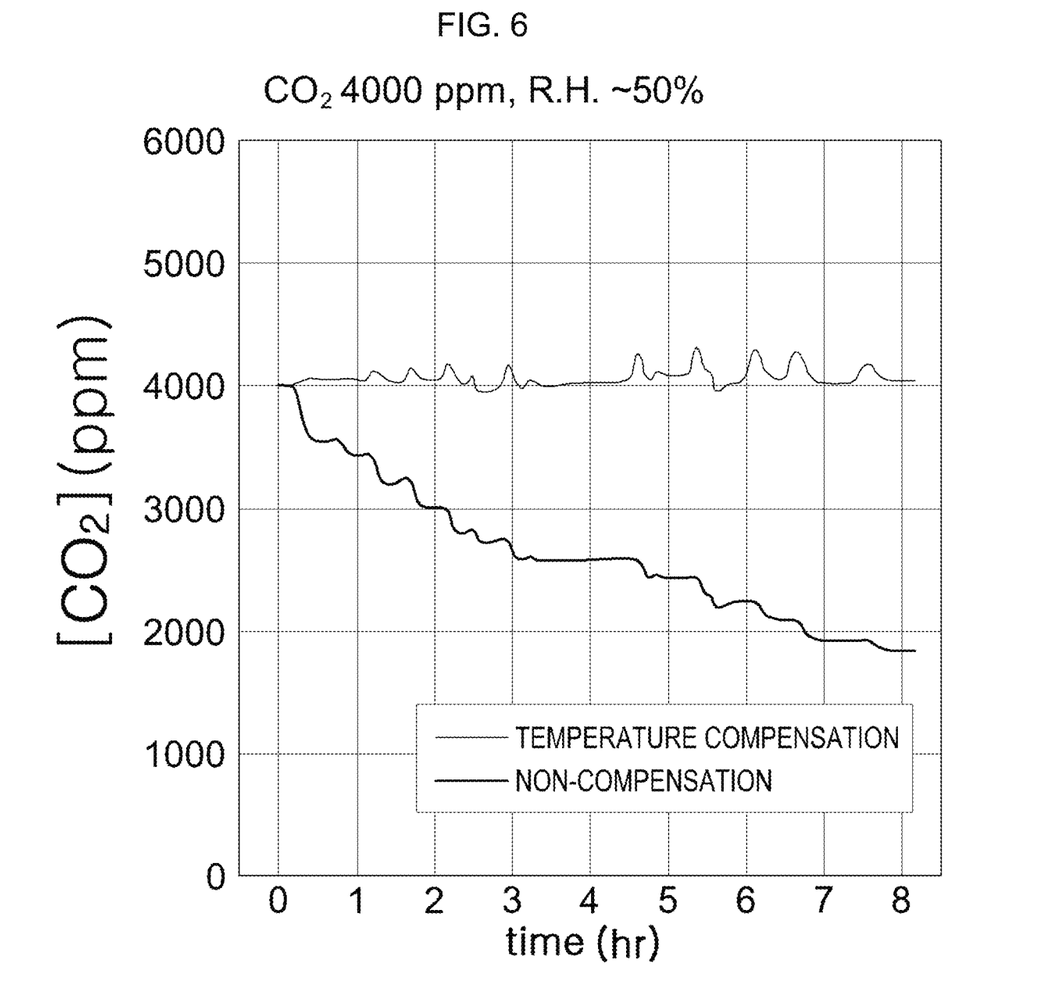
FIG. 6 illustrates the concentration of carbon dioxide compensated with the output voltage and the heater current according to the exemplary embodiment of the present invention.

FIG. 6 illustrates the concentration of carbon dioxide compensated with the output voltage and the heater current according to the exemplary embodiment of the present invention, and FIG. 7 illustrates the concentration of carbon dioxide compensated with the heater current according to the exemplary embodiment of the present invention.

In the first to third steps, the output voltage may be compensated with the change of the current of the heater 70, which is measured by the gas sensor module 1 regardless of the external temperature.

According to the exemplary embodiment of the present invention, the compensation method described in such a process may occur inside or outside the gas sensor module 1 and may include all device which enables the determination. That is, the compensation method may be implemented through the control device or the memory device, and also include an algorithm or a program including a control command.

For convenience in explanation and accurate definition in the appended claims, the terms "upper", "lower", "internal", "outer", "up", "down", "upwards", "downwards", "front", "rear", "back", "inside", "outside", "inwardly", "outwardly", "internal", "external", "forwards", and "backwards" are used to describe features of the exemplary embodiments with reference to the positions of such features as displayed in the figures.

The foregoing descriptions of specific exemplary embodiments the present invention have been presented for purposes of illustrative and description. They are not intended to be exhaustive or to limit the invention to the precise forms disclosed, and obviously many modifications and variations are possible in light of the above teachings. The exemplary embodiments were chosen and described to explain certain principles of the invention and their practical application, to enable others skilled in the art to make and utilize various exemplary embodiments of the present invention, as well as various alternatives and modifications thereof. It is intended that the scope of the invention be defined by the Claims appended hereto and their equivalents.

What is claimed is:

1. A temperature compensation method for a gas sensor module using a change of heater current, the method comprising:

a first step of deriving an output voltage equation of the gas sensor module from a cell reaction equation of an electrolyte and expressing the derived output voltage equation as an equation for a fluctuation temperature which varies depending on a sensor temperature and a compensation coefficient;

a second step of deriving the fluctuation temperature by a heater current indicating a current value of a heater formed in the gas sensor module and re-expressing the output voltage equation expressed in the first step as an equation for the heater current and the compensation coefficient; and a third step of measuring an output voltage depending on current of heaters at two or more points to determine the compensation coefficient of the output voltage equation re-expressed in the second step, wherein the output voltage measured in the third step is compensated with the change of the heater current measured by the gas sensor module regardless of an external temperature.

2. The method of claim 1, wherein in the first step, the cell reaction equation of the electrolyte is expressed by an electrode reaction energy equation to be derived to an equation associated with electrode reaction enthalpy or entropy.

3. The method of claim 1, wherein the second step includes:
- deriving fluctuation resistance of the heater depending on the fluctuation temperature, and
- deriving a relationship equation of the heater current and the output voltage by use of the fluctuation resistance.

4. The method of claim 1, wherein the third step includes determining a final compensation equation by substituting the compensation coefficient in the output voltage equation, and
- the output voltage which fluctuates is configured to be compensated by measuring the heater current changed depending on the fluctuation temperature through the final compensation equation.

5. The method of claim 1, wherein the output voltage is derived by a primary linear equation depending on the fluctuation temperature.

* * * * *